US010023611B2

(12) United States Patent
Puppala et al.

(10) Patent No.: US 10,023,611 B2
(45) Date of Patent: Jul. 17, 2018

(54) PROCESS FOR THE PREPARATION OF BORTEZOMIB MANNITOL ESTER

(71) Applicant: Cipla Limited, Mumbai (IN)

(72) Inventors: Ravikumar Puppala, Bangalore (IN); Srinivas Laxminarayan Pathi, Bangalore (IN); Dharmaraj Ramachandra Rao, Thane (IN); Rajendra Narayanrao Kankan, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 14/784,866

(22) PCT Filed: Apr. 16, 2014

(86) PCT No.: PCT/GB2014/000150
§ 371 (c)(1),
(2) Date: Oct. 15, 2015

(87) PCT Pub. No.: WO2014/170628
PCT Pub. Date: Oct. 23, 2014

(65) Prior Publication Data
US 2016/0075736 A1   Mar. 17, 2016

(30) Foreign Application Priority Data

Apr. 16, 2013  (IN) .......................... 1431/MUM/2013

(51) Int. Cl.
| C07K 5/06 | (2006.01) |
| A61K 38/05 | (2006.01) |
| A61K 31/69 | (2006.01) |
| C07F 5/02 | (2006.01) |
| A61K 31/444 | (2006.01) |
| A01N 43/48 | (2006.01) |

(52) U.S. Cl.
CPC .......... C07K 5/06191 (2013.01); A61K 31/69 (2013.01); A61K 38/05 (2013.01); C07F 5/025 (2013.01); A01N 43/48 (2013.01); A61K 31/444 (2013.01)

(58) Field of Classification Search
None
See application file for complete search history.

(56) References Cited

U.S. PATENT DOCUMENTS

| 4,499,082 A | 2/1985 | Shenvi et al. |
| 5,106,948 A | 4/1992 | Kinder et al. |
| 5,169,841 A | 12/1992 | Kleeman et al. |
| 5,187,157 A | 2/1993 | Kettner et al. |
| 5,242,904 A | 9/1993 | Kettner et al. |
| 5,250,720 A | 10/1993 | Kettner et al. |
| 5,780,454 A | 7/1998 | Adams et al. |
| 6,066,730 A | 5/2000 | Adams et al. |
| 6,083,903 A | 7/2000 | Adams et al. |
| 6,297,217 B1 | 10/2001 | Adams et al. |
| 6,699,835 B2 * | 3/2004 | Plamondon ............. C07F 5/025 514/21.9 |

FOREIGN PATENT DOCUMENTS

| IN | 2638MUM2012 | 9/2012 | |
| IN | 1431MUM2013 | 4/2013 | |
| WO | 9835691 A1 | 8/1998 | |
| WO | 9915183 A1 | 4/1999 | |
| WO | 02059130 A1 | 8/2002 | |
| WO | 02059131 A1 | 8/2002 | |
| WO | 2005097809 A2 | 10/2005 | |
| WO | WO2008075376 A1 * | 6/2008 | ............... C07F 5/02 |
| WO | 2009004350 A1 | 1/2009 | |
| WO | 2009036281 A2 | 3/2009 | |
| WO | WO2010039762 A2 * | 8/2010 | ............. A61K 31/69 |
| WO | 2010146172 A2 | 12/2010 | |
| WO | 2011087822 A1 | 7/2011 | |
| WO | 2011098963 A1 | 8/2011 | |
| WO | 2012048745 A1 | 4/2012 | |
| WO | 2014041324 A1 | 3/2014 | |
| WO | 2014170628 A1 | 10/2014 | |
| WO | 2014170628 A8 | 10/2014 | |

OTHER PUBLICATIONS

Byrn et al. Analysis of two commercially available bortezomib products: differences in assay of active agent and impurity profile. AAPS PharmSciTech. Jun. 2011;12(2):461-7.*
Brown et al. Organoboranes. 30. Convenient Procedures for the Synthesis of Alkyl- and Alkenylboronic Acids and Esters. Organometallics 1983, 2, 1311-1316.*
Foreign communication from a related counterpart application—International Search Report and Written Opinion, PCT/GB2014/000150, dated Jul. 16, 2014, 10 pages.
Foreign communication from a related counterpart application—International Preliminary Report on Patentability, PCT/GB2014/000150, dated Oct. 20, 2015, 8 pages.
Korcek, S., et al., "Absolute Rate Constants for the Autoxidation of Organometallic Compounds. Part II. Benzylboranes and 1-Phenylethylboranes;" J. Chem. Soc., Perkin Trans., 1972, pp. 242-248.

(Continued)

Primary Examiner — Marcela M Cordero Garcia
Assistant Examiner — Jia-Hai Lee
(74) Attorney, Agent, or Firm — Conley Rose, P.C.; Rodney B. Carroll

(57) ABSTRACT

A novel and improved process for preparation of bortezomib mannitol ester is derived, which process avoids excessive use of solvents, involves convenient, industrially feasible and economical techniques, and provides improvements in purity over processes known in the art.

18 Claims, 4 Drawing Sheets

(56) References Cited

OTHER PUBLICATIONS

Snyder, H.R., et al., "Aryl Boronic Acids. II. Aryl Boronic Anhydrides and their Amine Complexes," J. Am. Chem Soc., 1958, vol. 80, pp. 3611-3615.

* cited by examiner

PROCESS FOR THE PREPARATION OF BORTEZOMIB MANNITOL ESTER

CROSS-REFERENCE TO RELATED APPLICATIONS

This application is a filing under 35 U.S.C. 371 of International Application No. PCT/GB2014/000150 filed Apr. 16, 2014, entitled "Process for the Preparation of Bortezomib Mannitol Ester," which claims priority to Indian Patent Application No. 1431/MUM/2013 filed Apr. 16, 2013, which applications are incorporated by reference herein in their entirety.

TECHNICAL FIELD OF THE INVENTION

The present invention relates to a novel and improved process for preparation of bortezomib mannitol ester.

BACKGROUND OF THE INVENTION

Bortezomib is a modified dipeptidyl boronic acid derivative derived from leucine and phenyl alanine. The chemical name is [(1R)-3-methyl-1-[[(2S)-1-oxo-3-phenyl-2-[(pyrazinylcarbonyl)amino]propyl]amino]butyl] boronic acid and represented as follows:

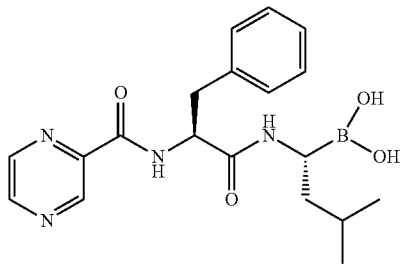 [SMILES: CC(C)C[C@H](NC(=O)[C@H](Cc1ccccc1)NC(=O)c1cnccn1)B(O)O]

Bortezomib is marketed as Velcade and Bortenat (generic), and is used to treat lymphomas.

The patent U.S. Pat. No. 5,780,454 discloses bortezomib, while WO2005097809 describes large scale preparation of bortezomib. There are other patent applications such as WO2009004350, WO2009036281, WO2010146172, WO2011087822, WO2011098963, WO2012048745 and IN patent application no. 2638/MUM/2012 which describe various processes for synthesis of bortezomib.

Boronic acid and its ester compounds display a variety of pharmaceutically useful biological activities. The patent U.S. Pat. No. 4,499,082 (1985) discloses peptide boronic acids as inhibitors of certain proteolytic enzymes. The patents U.S. Pat. No. 5,187,157 (1993), U.S. Pat. No. 5,242,904 (1993) and U.S. Pat. No. 5,250,720 (1993) describe a class of peptide boronic acids that inhibit trypsin-like proteases. The patents U.S. Pat. No. 5,169,841 (1992) discloses N-terminally modified peptide boronic acids that inhibit the action of rennin and U.S. Pat. No. 5,106,948 (1992), discloses certain tripeptide boronic acid compounds that inhibit the growth of cancer cells. The patents U.S. Pat. No. 5,780,454 (1998), U.S. Pat. No. 6,066,730 (2000), U.S. Pat. No. 6,083,903 (2000), and U.S. Pat. No. 6,297,217 (2001) relate to peptide boronic ester and acid compounds useful as proteasome inhibitors.

In the patent application WO9835691, it is described that proteasome inhibitors including boronic acid compounds are useful for treating infarcts such as those that occur during stroke or myocardial infarction. WO9915183 describes that proteasome inhibitors are useful for treating inflammatory and autoimmune diseases. Moreover, alkylboronic acids are relatively difficult to obtain in analytically pure form. Snyder et al., *J: Am. Chew. Soc.*, 3611 (1958), teaches that alkyl-boronic acid compounds readily form boroxines (anhydrides) under dehydrating conditions and their boroxines are often air-sensitive. Korcek et al., *J. Chem. Soc., Perkin Trans.* 2 242 (1972), teaches that butylboronic acid is readily oxidized by air to generate 1-butanol and boric acid. These difficulties were limiting the pharmaceutical utility of boronic acid compounds.

Bortezomib (a boronic acid compound), in its solid state as a pure API existed in the form of highly water insoluble boroxine, a cyclic boronic acid anhydride. When placed in water, the boroxine dissociated to form equilibrium between itself and the monomeric bortezomib resulting in an apparent water solubility of about 0.5-1 mg/ml which was not sufficient for formulation purposes. In order to deal with such issues, the innovator company in their patent WO2002059130 application has described a stable formulation containing mannitol ester of bortezomib. The application '9130 also relates to a process of preparing such formulation by first dissolving the bortezomib in warm (temperature around 45±2° C.) TBA (tertiary butyl alcohol), then adding water and mannitol (1% bulking agent), followed by freeze drying. On reconstitution, Bortezomib was found to rapidly dissolve and more soluble in water due to the in situ formation of boronic acid esters by reaction with diol groups of mannitol during the alcohol lyophilisation or freeze-drying process. So, the FDA approved drug Bortezomib is now available as a mannitol boronic ester which in its reconstituted form consists of the mannitol ester in equilibrium with its hydrolysis product, the monomeric boronic acid. The drug substance exists in its cyclic anhydride from as a trimeric boroxine, as described below in FIG. 1.

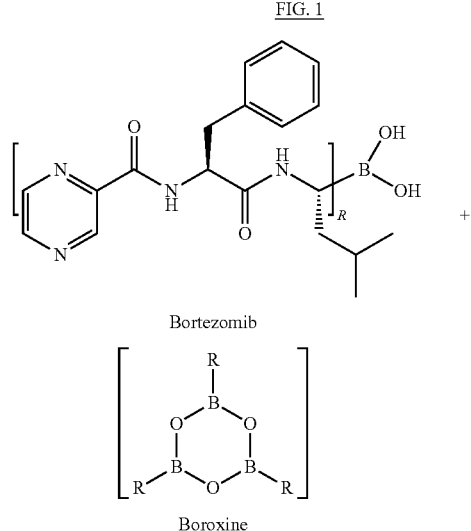

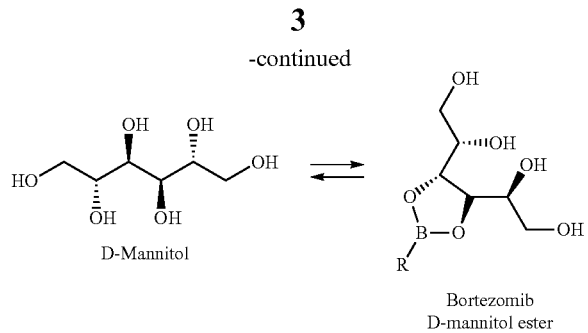

D-Mannitol

Bortezomib
D-mannitol ester

However, this process of making Bortezomib mannitol ester as mentioned in the prior art has certain limitations like, a) involves a step of freeze-drying or alcohol lyophilisation which requires the use of very expensive refrigeration-drying machine or freeze-dryer or alcohol lyophiliser, that makes the process an economical liability on pharmaceutical companies while manufacturing Bortezomib mannitol ester on an industrial scale; b) involves use of large quantities of TBA (tertiary butyl alcohol) as one of the solvents, that results into formation of unstable butylboronic acid which is readily oxidized in air; c) a much complicated process; and d) involves a process that uses larger volumes of water and is carried out at a higher temperature, which may result in formation of a larger amount of degradation impurity (X), as depicted in the reaction below,

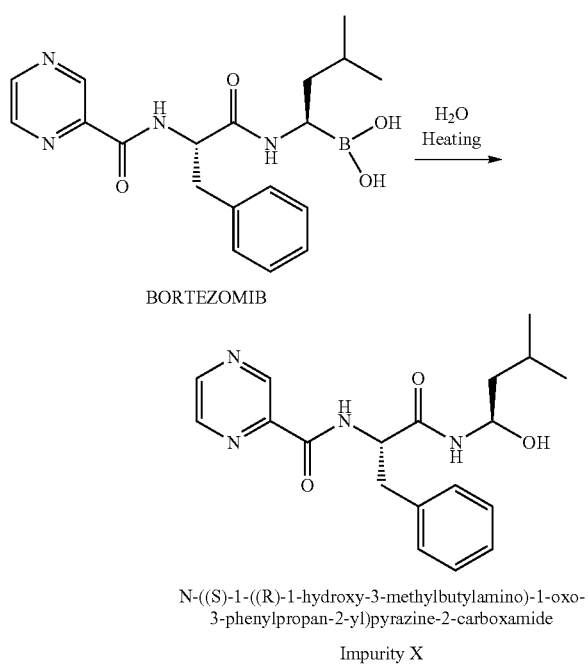

BORTEZOMIB

N-((S)-1-((R)-1-hydroxy-3-methylbutylamino)-1-oxo-3-phenylpropan-2-yl)pyrazine-2-carboxamide Impurity X There is thus a need in the art for an improved process for preparing Bortezomib mannitol esters. Ideally, such improved processes should be convenient, industrially feasible, and economical which at the same time should provide good yield, chemical stability, pure product substantially free of impurities and easily accessible treatment to a subject in need of boronic acid therapy.

SUMMARY OF THE INVENTION

The present invention provides an industrially advantageous process for preparation of bortezomib-mannitol ester which avoids drawbacks associated with the prior art processes. The bortezomib-mannitol ester prepared by the process of the invention is substantially free of degradation impurity X. Thus, the present invention also provides substantially pure bortezomib-mannitol ester.

In a first aspect the present invention provides a process for the preparation of bortezomib-mannitol ester (compound B)

(compound B)

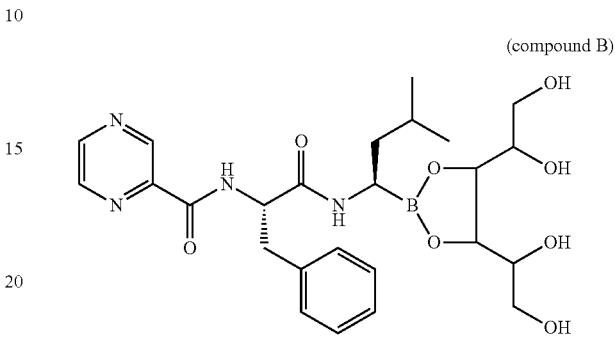

that involves a simple chemical reaction, the reaction comprising:
(a) dissolving bortezomib (compound A)

(compound A)

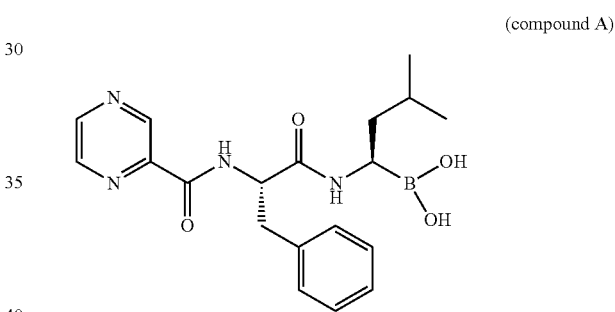

in a first solvent to form a first solution;
(b) adding mannitol to the first solution;
(c) removing the first solvent from the first solution to form a residue comprising bortezomib-mannitol ester;
(d) adding a second solvent to the residue to form a suspension of bortezomib-mannitol ester in the second solvent; and
(e) isolating the bortezomib-mannitol ester from the second solvent.

In a second aspect the present invention provides bortezomib-mannitol ester prepared by a process of the present invention.

In a third aspect the present invention provides sterile non-lyophilized bortezomib-mannitol ester.

In a fourth aspect the present invention provides sterile non-lyophilized bortezomib-mannitol ester prepared by a process of the present invention.

In a fifth aspect the present invention provides a pharmaceutical composition comprising bortezomib-mannitol ester.

In a sixth aspect the present invention provides a pharmaceutical composition comprising bortezomib-mannitol ester prepared by a process of the present invention.

In a seventh aspect the present invention provides a pharmaceutical composition comprising sterile non-lyophilized bortezomib-mannitol ester prepared by a process of the present invention.

In an eighth aspect the present invention provides bortezomib-mannitol ester prepared by a process of the present invention for use in treating or preventing relapsed multiple myeloma and mantle cell lymphoma.

In a ninth aspect the present invention provides sterile non-lyophilized bortezomib-mannitol for use in treating or preventing relapsed multiple myeloma and mantle cell lymphoma.

In a tenth aspect the present invention provides a method of treating or preventing relapsed multiple myeloma and mantle cell lymphoma comprising administering to a patient in need thereof bortezomib-mannitol ester prepared by a process of the present invention.

In an eleventh aspect the present invention provides a method of treating or preventing relapsed multiple myeloma and mantle cell lymphoma, comprising administering to a patient in need thereof sterile non-lyophilized bortezomib-mannitol ester by a process of the present invention.

In a twelfth aspect the present invention provides a use of bortezomib-mannitol ester of the invention for the manufacture of a medicament for the treatment or prevention of relapsed multiple myeloma and mantle cell lymphoma in a patient.

In a thirteenth aspect the present invention provides a use of sterile non-lyophilized bortezomib-mannitol ester of the invention for the manufacture of a medicament for the treatment or prevention of relapsed multiple myeloma and mantle cell lymphoma in a patient.

Further features are defined in the dependent claims.

"Substantially pure bortezomib-mannitol ester" may be defined as bortezomib-mannitol ester having about 0.3% by weight of impurity X or less, preferably about 0.2% by weight of impurity X or less, more preferably about 0.1% by weight of impurity X or less.

As used herein, the term "residue" is defined to mean the material left behind after the first solvent is removed from the first solution. In an aspect, the residue comprises of bortezomib-mannitol ester, although other substances may be present in small amounts, such as mannitol, free bortezomib and the trimetric boroxine form of bortezomib.

As used herein, the term "sterilisation" is defined to mean a process that renders the first solution sterile, by removing any life form or any pathological agent from the first solution, such as fungi, bacteria, viruses, or any other microorganism. After such sterilisation, the first solution is rendered free of any agent capable of causing an infection in a patient. Sterilisation by filtration involves the physical removal of such life forms or pathological agents from a solution, which are not occluded since they are not able to pass through the pores of the filter.

Bortezomib-mannitol ester is referred to hereinafter as "compound B".

In an aspect the present invention provides sterile non-lyophilized bortezomib-mannitol ester. The sterile non-lyophilized bortezomib-mannitol ester prepared by the process of the invention is substantially free of degradation impurity X. Thus, the present invention also provides substantially pure sterile non-lyophilized bortezomib-mannitol ester.

As used herein, the term "non-lyophilized bortezomib-mannitol ester" means bortezomib-mannitol ester which has not been subjected to lyophilisation, or was not lyophilised. The process of lyophilisation would comprise freezing a solution of bortezomib-mannitol ester, and subjecting a frozen solution to reduced pressure, thus in one aspect, the term may also mean a bortezomib-mannitol ester prepared by a process where a solution of the bortezomib-mannitol ester was not frozen.

"Substantially pure sterile non-lyophilized bortezomib-mannitol ester" may be defined as sterile non-lyophilized bortezomib-mannitol ester having about 0.3% by weight of impurity X or less, preferably about 0.2% by weight of impurity X or less, more preferably about 0.1% by weight of impurity X or less.

In an aspect the present invention provides a process for preparation of sterile non-lyophilised bortezomib-mannitol ester, wherein the process comprises:
(a) dissolving bortezomib (compound A) into a first solvent to form a solution;
(b) filtering the solution through 0.45 micron filter followed by 0.22 micron filter in a sterile area;
(c) adding sterile mannitol to the solution;
(d) removing the solvent by distillation;
(e) adding a second solvent to the residue;
(f) stirring, filtering and drying the sterile non-lyophilised bortezomib-mannitol ester.

Bortezomib may form esters with polyols comprising two hydroxyl groups on adjacent carbon atoms. In an aspect, the polyol is a sugar alcohol or a reduced sugar. In a preferred aspect, the sugar alcohol or reduced sugar is selected from mannitol, sorbitol or xylitol. Either the racemate, D- or L-form of mannitol, sorbitol or xylitol may be used. More preferably, the reduced sugar moiety is mannitol. Whilst racemic of mannitol or L-mannitol may be used, D-mannitol is particularly preferred. The structure of bortezomib-mannitol ester, where the mannitol is D-mannitol, is shown below.

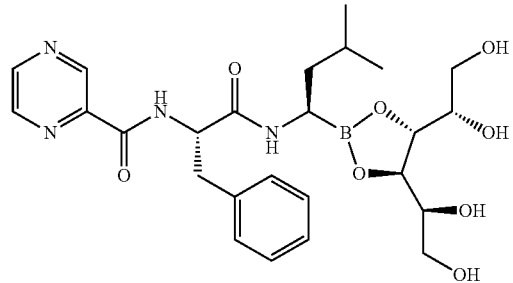

Bortezomib D-mannitol ester

In another aspect, a sugar may be used to form an ester with bortezomib. Preferably, the sugar is selected from fructose, glucose or sucrose.

An advantage of the process of the present invention is that excessive use of solvents is avoided or minimised.

Other advantages of the present invention include the use of a convenient, industrially feasible and economical vacuum drying method, which avoids the expensive alcohol lyophilisation process as reported in the prior art. Avoiding lyophilisation can itself contribute to huge cost-reductions when preparing bortezomib-mannitol ester on an industrial scale.

The present invention is also advantageous in that the esterification process is efficient, in that it avoids the drawbacks associated with reported prior art processes as confirmed by comparative NMR study between bortezomib-mannitol ester compound formed by the process of the present invention and the two commercially available bortezomib products (i.e. Bortenat and VELCADE), based on the evaluation of boronic acid to boronic ester ratio in respective samples.

During the step of forming the ester, the process of the present invention may not involve the use of water, and may be conducted at a much lower temperature, thus resulting in the formation of a pure product substantially free of the degradation impurity X, i.e. N—((S)-1-((R)-1-hydroxy-3-methylbutylamino)-1-oxo-3-phenylpropan-2-yl)pyrazine-2-carboxamide.

The bortezomib mannitol ester formed according to the present invention exhibits an increased solubility of the drug bortezomib in water.

In the following aspects of the invention, the substantially pure bortezomib-mannitol ester (including sterile non-lyophilised bortezomib-mannitol ester) are preferably prepared by the processes as described herein.

In a further aspect of the invention there is provided a pharmaceutical composition comprising substantially pure bortezomib-mannitol ester (including sterile non-lyophilised bortezomib-mannitol ester), together with one or more pharmaceutically acceptable excipients. The pharmaceutical compositions of the invention may be prepared according to methods known in the art. The suitable pharmaceutically acceptable excipients for inclusion in such pharmaceutical compositions would be known to those skilled in the art.

According to another aspect of the invention, there is provided use of a pharmaceutical composition of the invention in the manufacture of a medicament for the treatment of relapsed multiple myeloma and mantle cell lymphoma.

According to another aspect of the invention, there is provided a method of treating a subject with relapsed multiple myeloma and mantle cell lymphoma, wherein the method comprises administering a bortezomib-mannitol ester (including sterile non-lyophilised bortezomib-mannitol ester) according to the present invention to a patient in need thereof.

DETAILED DESCRIPTION OF THE INVENTION

Figure 1:
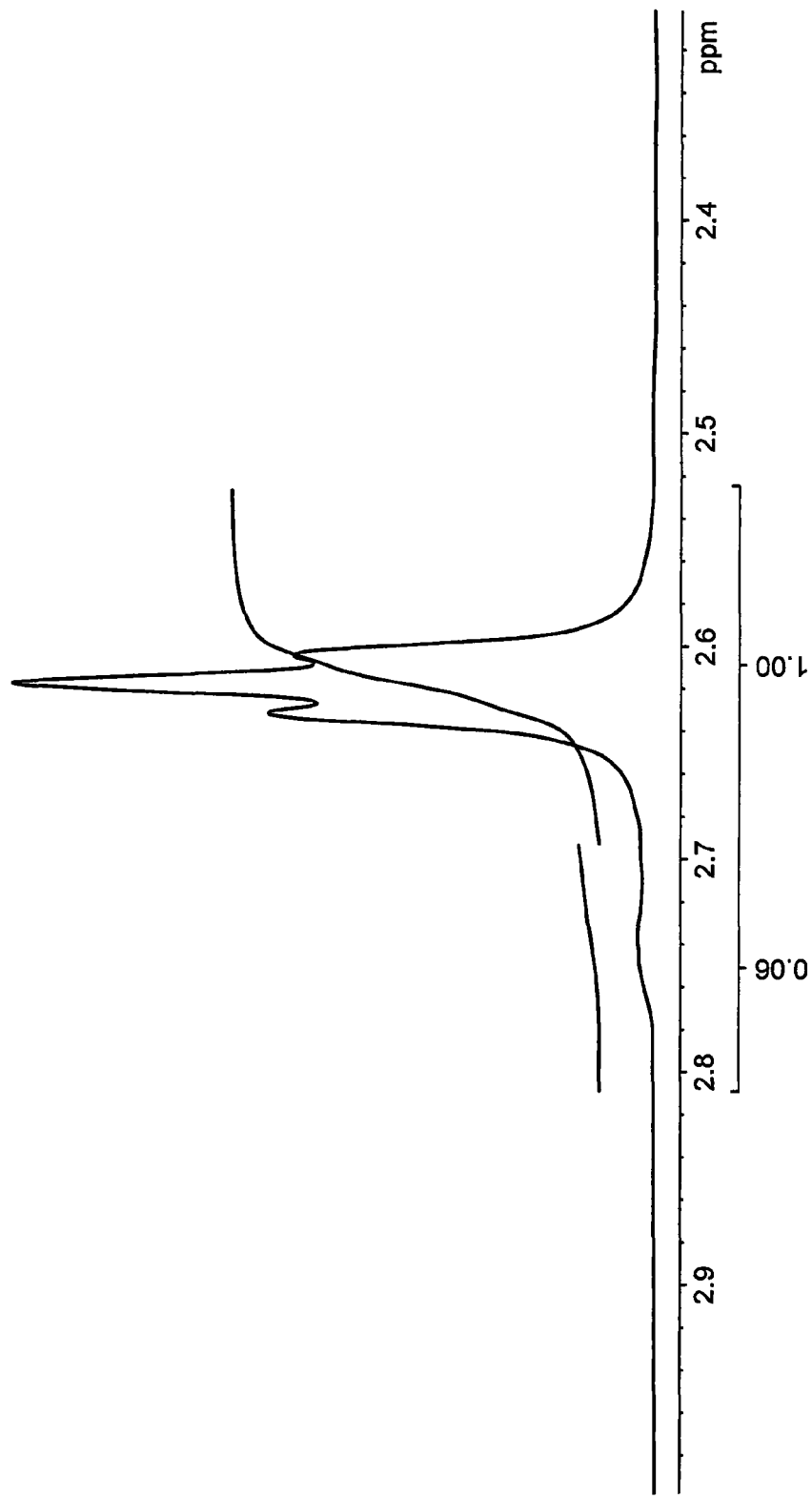
FIGS. 1 and 2 each show 1D $^1$H-nuclear magnetic resonance (NMR) spectra of two samples of bortezomib-mannitol ester prepared in accordance with the present invention. Details regarding the NMR acquisition parameters are provided in example 7.

The inventors of the present invention have developed a novel and improved process for preparation of bortezomib-mannitol ester (hereinafter referred to as "compound B") from bortezomib (hereinafter referred to as "compound A").

The process of the invention results in the formation of compound B substantially free of degradation impurity X. As used herein, the term "substantially free of degradation impurity X" refers to bortezomib-mannitol ester having about 0.3% by weight of impurity X or less, preferably about 0.2% by weight of impurity X or less, more preferably about 0.1% by weight of impurity X or less. The impurity X related to bortezomib-mannitol ester as determined by high performance liquid chromatography (HPLC).

According to an aspect of the present invention, there is provided a process for the preparation of compound B that comprises;
(a) dissolving bortezomib (compound A) into a first solvent to form a solution;
and adding mannitol to the solution;
(b) removing the solvent by distillation;
(c) adding a second solvent to the residue;
(d) stirring, filtering and drying the bortezomib-mannitol ester.

Compound A used as a starting material may be prepared by the processes known in the prior art, for example as per the process described in the IN patent application No. 2638/MUM/2012, and in WO 14/041324, which are both incorporated herein by reference in their entirety.

The process for preparation of compound B may comprise reacting compound A with a reduced sugar moiety, like mannitol, wherein mannitol is preferably of D-configuration.

In accordance with the present invention, the process may comprise of adding compound A in a first solvent selected from methanol, isopropyl alcohol, ethanol, methylene dichloride, ethyl acetate and tetrahydrofuran, or any mixture thereof, that can be used in place of TBA (tertiary butyl alcohol) used by the prior art, to obtain a chemically stable compound B. A large amount of TBA is required to dissolve bortezomib, which is undesirable from both a cost perspective and disposal concerns. Use of TBA also involves a higher temperature in order to dissolve the bortezomib, as well as the use of water, which are thought to favour the formation of impurities such as impurity X. The solvents used in accordance with the present invention solves these problems associated with the TBA.

An example of the novel process of preparing compound B is as depicted in scheme I:

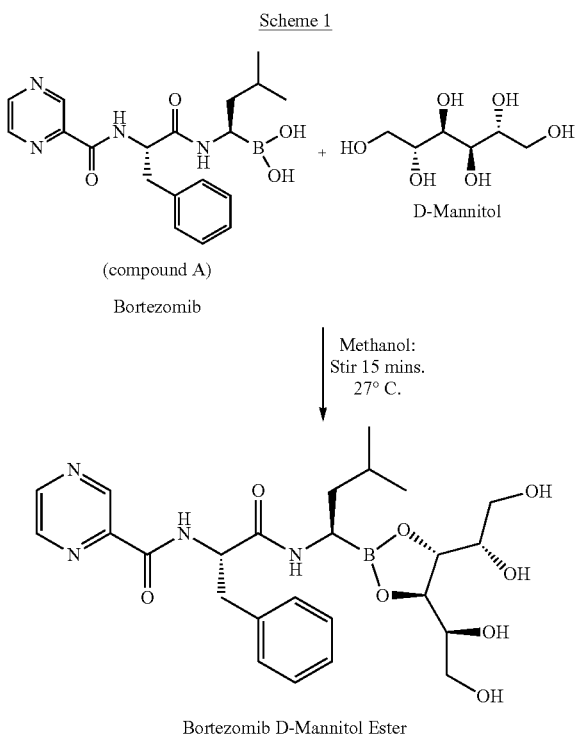

In an aspect of the present invention, the process for preparing compound B comprises treating compound A with mannitol in a first solvent, without involving water, at a preferably lower temperature of 27±2° C., that thereby obtain the formation of compound B substantially free of the degradation impurity X.

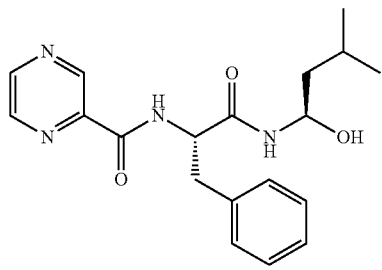

Impurity X

N-((S)-1-((R)-hydroxy-3-methylbutylamino)-1-oxo-
3-phenylpropan-2-yl)pyrazine-2-carboxamide The temperature for reaction is preferably 27±2° C., but it will be appreciated that other temperatures may be used, including less than 30° C., less than 31° C., less than 32° C., less than 33° C., less than 34° C., less than 35° C., less than 36° C. or less than 37° C. The temperature is preferably higher than 10° C.

The decreased levels of impurity X provided by the present invention is confirmed by the following comparative HPLC data, as depicted in the Table 1.

TABLE 1

| Sl. No. | Process | Purity | Degradation Impurity (X) |
|---|---|---|---|
| 1 | As per the process described in the patent application WO2002059130 | 98.40% | 0.41% |
| 2 | As per the process described in this present invention | 99.56% | 0.05% |

The reaction time is preferably 15 minutes, but it will be appreciated that longer reaction times may be used, including less than 17 minutes, less than 19 minutes, less than 19 minutes, less than 20 minutes, less than 21 minutes, less than 23 minutes, less than 25 minutes, less than 27 minutes, less than 29 minutes, or less than 30 minutes. The reaction time is preferably longer than 5 minutes.

The process of the present invention is particularly advantageous as it avoids the much expensive and time consuming freeze-drying or alcohol lyophilisation of compound B; instead may use a simpler, convenient, industrially feasible and economical vacuum drying process.

A solid form of compound B is produced when compound A is treated with mannitol in a first solvent. The first solvent is preferably polar. Suitable polar solvents include methanol, isopropyl alcohol, ethanol, methylene dichloride, ethyl acetate, tetrahydrofuran, and mixtures thereof.

The first solvent is preferably substantially free of water. The term "substantially free of water" as used herein means less than 5%, less than 4%, less than 3%, less than 2%, less than 1%, less than 0.5%, less than 0.4%, less than 0.3%, less than 0.2%, less than 0.1%, less than 0.05%, or 0% [all percentages in (v/v)]. It will be appreciated that very small amounts of water may be present in the first solvent; however, such small amounts should be avoided where possible, and where a small amount is present, it is incidental, and its presence unintentional.

The process further comprises adding a second solvent to the residue to form a suspension of bortezomib-mannitol ester in the second solvent, and isolating the bortezomib-mannitol ester from the second solvent.

The second solvent is preferably water immiscible. More preferably, the second solvent used is selected from the group consisting of: n-heptane, hexane, toluene, cyclohexane, diisopropyl ether, diethyl ether, and any combination thereof. The second solvent is preferably substantially free of water.

The process further comprises removing the first solvent from the first solution to form a residue comprising bortezomib-mannitol ester. Removal of the first solvent is preferably carried out by evaporating the first solvent from the first solution, for instance by heating or distilling the first solvent, and/or subjecting the first solution to a reduced pressure (such as a pressure less than 1 atmosphere).

The reduced pressure is pressure is less than 1 atmosphere. The pressure may be less than 0.8 atmospheres, 0.6 atmospheres, 0.4 atmospheres, 0.3 atmospheres, 0.2 atmospheres, 0.1 atmospheres, 0.05 atmospheres, or 0.02 atmospheres. The pressure is preferably higher than 0.01 atmospheres.

The temperature at which the first solvent is evaporated is preferably lower than ambient temperature, i.e. 30°. More preferably the temperature is less than 28° C., 26° C., 25° C., 24° C., 23° C., or 22° C. A temperature higher than 10° C. is preferred.

In an aspect, isolation of compound B may be carried out by filtering the solid. The filtrate may be washed with an amount of the second solvent. The solid is preferably dried under vacuum at 43±2° C., but other temperatures may be used, including than 47° C., less than 49° C., less than 51° C., less than 53° C., less than 55° C. or less than 57° C. The temperature is preferably higher than 20° C.

Compound B (bortezomib-mannitol ester) obtained in accordance with the present invention advantageously shows better water solubility i.e. soluble in around 5 volumes water, than the poorly water soluble drug bortezomib.

A further advantage of the present invention is to provide compound B with low levels of free boronic acid. In particular, the present invention provides a product where the ratio of bortezomib-mannitol ester to bortezomib is greater than 1:0.09, preferably greater than 1:0.08, and most preferably greater than 1:0.07.

The process of the invention results in the formation of compound C substantially free of degradation impurity X. As used herein, the term "substantially free" refers to bortezomib-mannitol ester having about 0.3% by weight of impurity X or less, preferably about 0.2% by weight of impurity X or less, more preferably about 0.1% by weight of impurity X or less.

The impurity X related to bortezomib mannitol ester may be determined by high performance liquid chromatography (HPLC).

In another aspect the present invention provides sterile non-lyophilised bortezomib-mannitol ester.

According to an aspect of the present invention, there is provided a process for the preparation of sterile non-lyophilised bortezomib-mannitol ester that comprises;
(a) dissolving bortezomib (compound A) into a first solvent to form a solution;
(b) filtering the solution through 0.45 micron filter followed by 0.22 micron filter in a sterile area;

(c) adding sterile mannitol to the solution;
(d) removing the solvent by distillation;
(e) adding a second solvent to the residue;
(f) stirring, filtering and drying the sterile non-lyophilised bortezomib-mannitol ester.

The first solution may be sterilised by filtration. This can be achieved by passing the first solution through a sub-micron filter, such as a 0.22 micron filter. The first solution may optionally be passed through a 0.45 micron filter, which may assist in removing larger insoluble matter from the first solution, and thus decreasing the chance of blocking the 0.22 micron filter. Filters with even smaller pore sizes may be used, such as those with 50 nm, or 20 nm, if desired.

The present invention also relates to an advantageous process of preparing bortezomib-mannitol ester as depicted in scheme 1, which being a chemically induced process may increase the scope of introducing variables or specific functional groups at certain structural positions of the drug ester, which can further open a new route of investigation of structural modifications of bortezomib-mannitol esters by subsequently monitoring their activities.

According to the present invention, there is provided a pharmaceutical composition comprising the bortezomib-mannitol ester of the present invention, with one or more pharmaceutically acceptable excipients.

According to the present invention, there is also provided a process of preparing the pharmaceutical composition comprising bortezomib-mannitol ester of the present invention along with pharmaceutically acceptable excipients.

EXAMPLES

Example 1: Preparation of Compound B

In a round bottomed flask, 1.0 gram of bortezomib was added to 20 ml of methanol. The mixture was stirred until dissolution of the solid bortezomib. To this solution 5.0 grams of D-mannitol was added and the reaction mixture was stirred continuously for 15 minutes at a temperature of 27±2° C. This was followed by distillation process by which the solvent methanol was completely distilled under vacuum at below 25° C. 50 ml of n-heptane was then charged and continuous stirring was carried out for 30 minutes. The product obtained was then filtered and washed with n-heptane. The solid was then exposed to drying process under vacuum at 43±2° C., to get the final compound B.
Dry Weight: 5.5 grams
Purity: 99.36%
LOD: 0.65%

Example 2: Preparation of Compound B

In a round bottomed flask, 1.0 gram of bortezomib was added to 20 ml of methanol. The mixture was stirred until dissolution of the solid bortezomib. To this solution 8.0 grams of D-mannitol was added and the reaction mixture was stirred continuously for 15 minutes at a temperature of 27±2° C. This was followed by distillation process by which the solvent methanol was completely distilled under vacuum at below 25° C. 50 ml of n-heptane was then charged and continuous stirring was carried out for 30 minutes. The product obtained was then filtered and washed with n-heptane. The solid was then exposed to drying process under vacuum at 43±2° C., to get the final compound B.
Dry Weight: 8.5 grams
Purity: 99.33%
LOD: 0.32%

Example 3: Preparation of Compound B

In a round bottomed flask, 1.0 gram of bortezomib was added to 20 ml of methanol. The mixture was stirred until dissolution of the solid bortezomib. To this solution 2.0 grams of D-mannitol was added and the reaction mixture was stirred continuously for 15 minutes at a temperature of 27±2° C. This was followed by distillation process by which the solvent methanol was completely distilled under vacuum at below 25° C. 50 ml of n-heptane was then charged and continuous stirring was carried out for 30 minutes. The product obtained was then filtered and washed with n-heptane. The solid was then exposed to drying process under vacuum at 43±2° C., to get the final compound B.
Dry Weight: 2.8 grams
Purity: 99.46%
LOD: 0.96%

Example 4: Preparation of Compound B

In a round bottomed flask, 1.0 gram of bortezomib was added to 100 ml of ethanol. The mixture was stirred until dissolution of the solid bortezomib. To this solution 5.0 grams of D-mannitol was added and the reaction mixture was stirred continuously for 15 minutes at a temperature of 27±2° C. This was followed by distillation process by which the solvent ethanol was completely distilled under vacuum at below 25° C. 50 ml of n-heptane was then charged and continuous stirring was carried out for 30 minutes. The product obtained was then filtered and washed with n-heptane. The solid was then exposed to drying process under vacuum at 43±2° C., to get the final compound B.
Dry Weight: 5.3 grams Example 5: Preparation of Compound B In a round bottomed flask, 1.0 gram of bortezomib was added to 10 ml of methylene chloride The mixture was stirred until dissolution of the solid bortezomib. To this solution 5.0 grams of D-mannitol was added and the reaction mixture was stirred continuously for 15 minutes at a temperature of 27±2° C. This was followed by distillation process by which the solvent methylene chloride was completely distilled under vacuum at below 25° C. 50 ml of n-heptane was then charged and continuous stirring was carried out for 30 minutes. The product obtained was then filtered and washed with n-heptane. The solid was then exposed to drying process under vacuum at 43±2° C., to get the final compound B.
Dry Weight: 5.5 grams Example 6A: Preparation of Compound B In a round bottomed flask, 1.0 gram of bortezomib was added to 20 ml of isopropyl alcohol. The mixture was stirred until dissolution of the solid bortezomib. To this solution 5.0 grams of D-mannitol was added and the reaction mixture was stirred continuously for 15 minutes at a temperature of 27±2° C. This was followed by distillation process by which the solvent methanol was completely distilled under vacuum at below 25° C. 50 ml of n-heptane was then charged and continuous stirring was carried out for 30 minutes. The product obtained was then filtered and washed with n-hep tane. The solid was then exposed to drying process under vacuum at 43±2° C., to get the final compound B.
Dry Weight: 5.3 grams

Example 6B: Preparation of Sterile Non-Lyophilized Bortezomib-Mannitol Ester The following operation was carried in a sterile area in its entirety. In round bottom flask, 1.0 gram of bortezomib was added to 20 ml of methanol and the mixture was stirred to clear solution. The clear solution was filtered through a 0.45 micron filter followed by a 0.22 micron filter in the sterile area. To this clear filtrate was added 10.0 gram of sterile D-mannitol and the contents were stirred for 15 min at 27±2° C. Methanol was distilled completely under vacuum below 25° C. 50 ml of filtered n-heptane was added and stirred for 30 min. The product obtained was filtered and washed with filtered n-heptane. The solid was then exposed to drying process under vacuum at 43±2° C. and packed in sterile bags.

Example 7: NMR Analysis of Compound B

Compound B formed in accordance with the invention was analysed using NMR.

1D $^1$H-nuclear magnetic resonance (NMR) analysis was performed by dissolving compound B in approximately 0.7 mL solution of 0.9% NaCl (w/v) in 10% $D_2O$/90% $H_2O$ (v/v) on a Varian 500 MHz NMR spectrometer using following parameters to determine a boronic acid to boronic ester ratio.

Parameter Details:
1. Spectral width: −2 ppm to 18 ppm
2. Acquisition time: 3 s
3. Number of scans: 64
4. Pulse width: 7.4 μs
(PRESAT Mode used to suppress the water peak resonate at 4.8 ppm)

1D $^1$H & $^{13}$C nuclear magnetic resonance (NMR) analysis was also performed by dissolving compound B in DMSO-d6 solvent to confirm the ester formation between bortezomib and D-mannitol.

Figure 2:
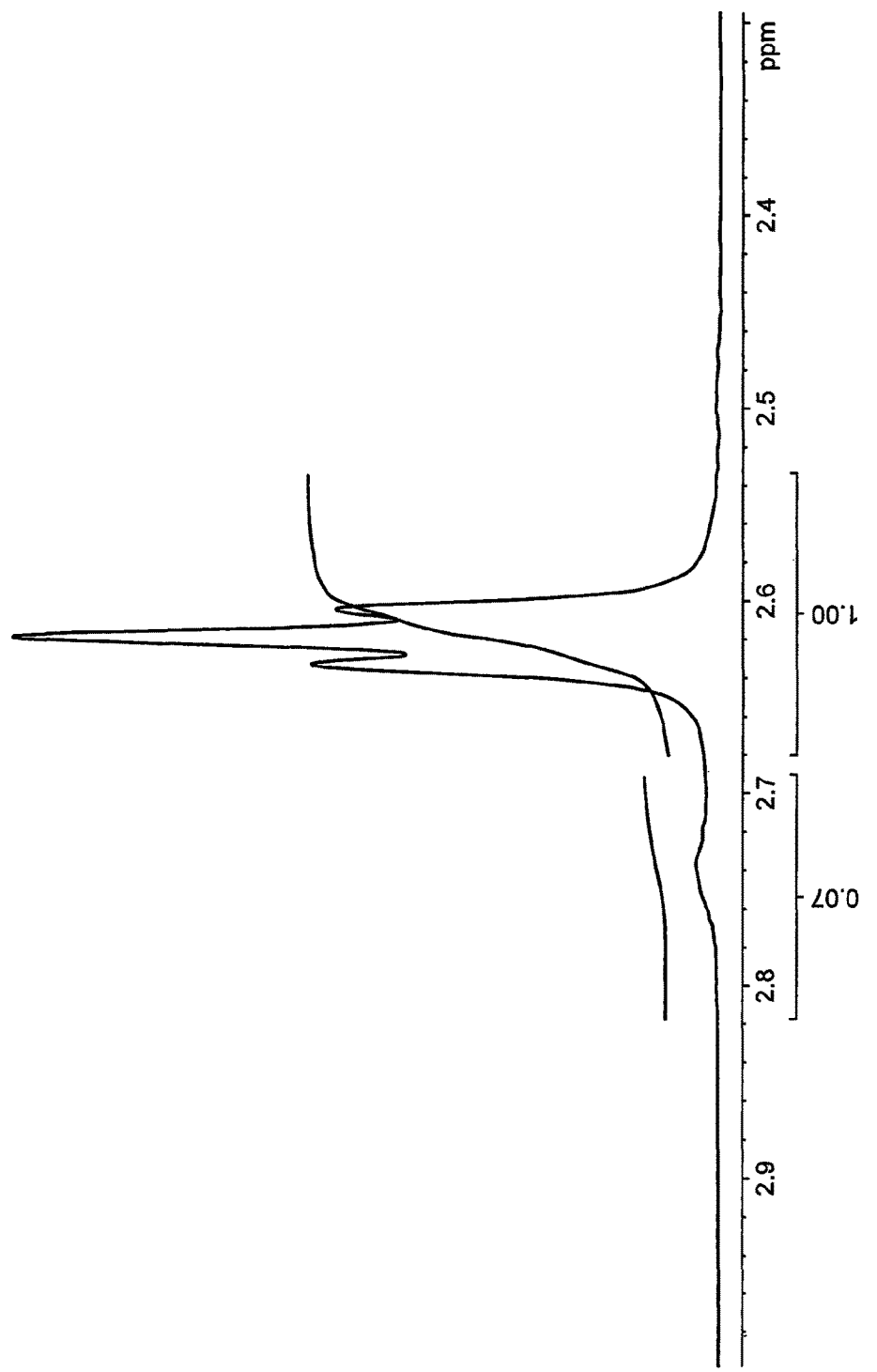

The $^1$H NMR spectrum recorded in duplicate revealed a boronic acid (i.e. bortezomib) to boronic ester (i.e. bortezomib-mannitol ester) ratio of approximately 0.06:1 and 0.07:1, as depicted in the FIG. 1 and FIG. 2, respectively. The region from 2.35 to 2.85 ppm represents the integrated signal from the protons of free bortezomib and ester wherein the peak at ~2.73 ppm is assigned to the free bortezomib and the peak at ~2.62 ppm is assigned to the bortezomib-mannitol ester.

Following are the results of free bortezomib to bortezomib-mannitol ester ratio reported in the art for Bortenat and VELCADE samples and the one for compound B.

| Sample Details | free bortezomib:bortezomib-mannitol ester ratio |
|---|---|
| Bortenat 2 mg | 0.27:1 |
| Bortenat 3.5 mg | 0.13:1 |
| VELCADE | 0.10:1 |
| Compound B | 0.07:1 |

Figure 3:
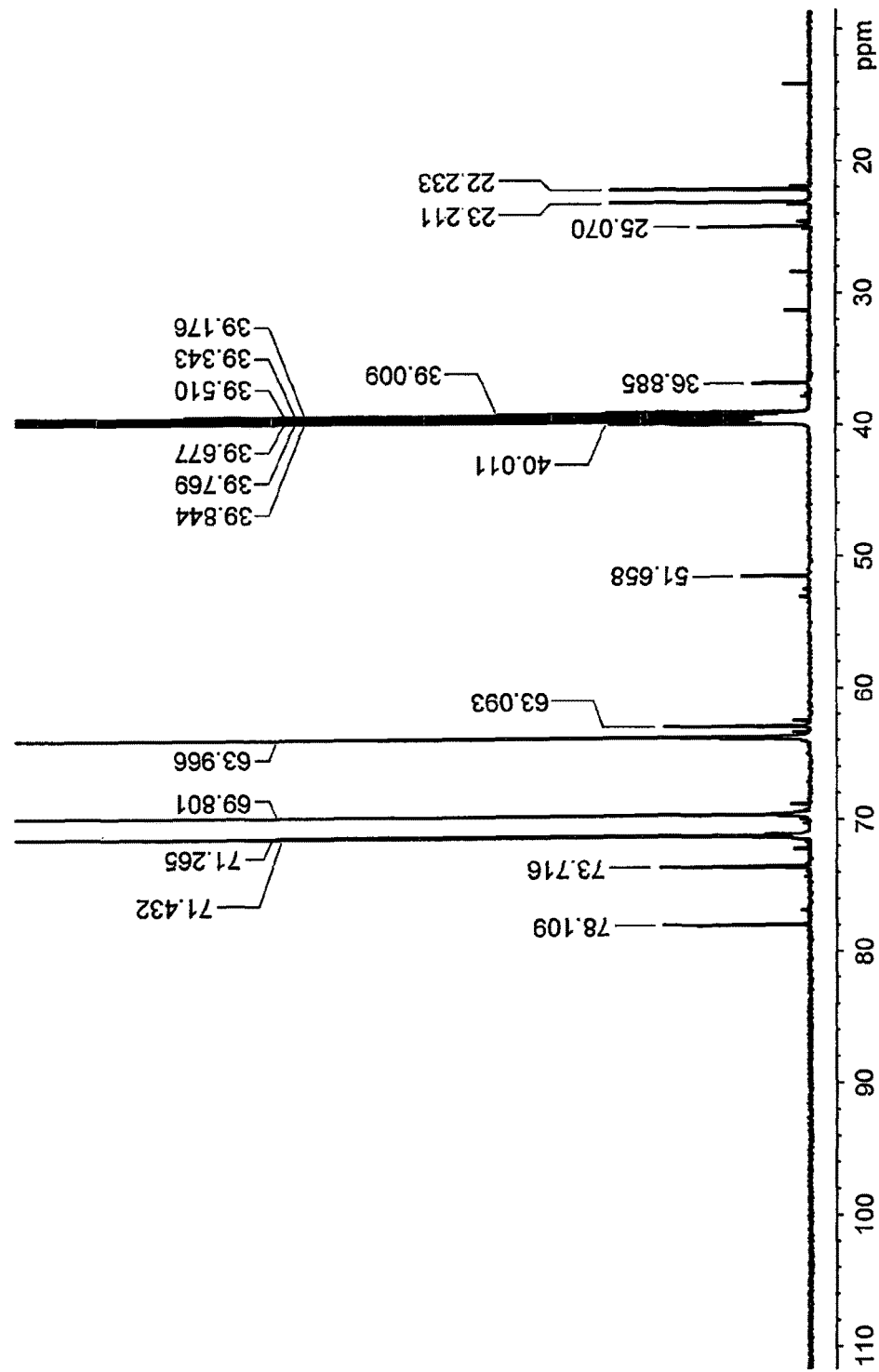
FIG. 3 shows the $^{13}$C NMR spectrum of a sample of bortezomib-mannitol ester prepared in accordance with the present invention, between 0 to 110 ppm.
Figure 4:
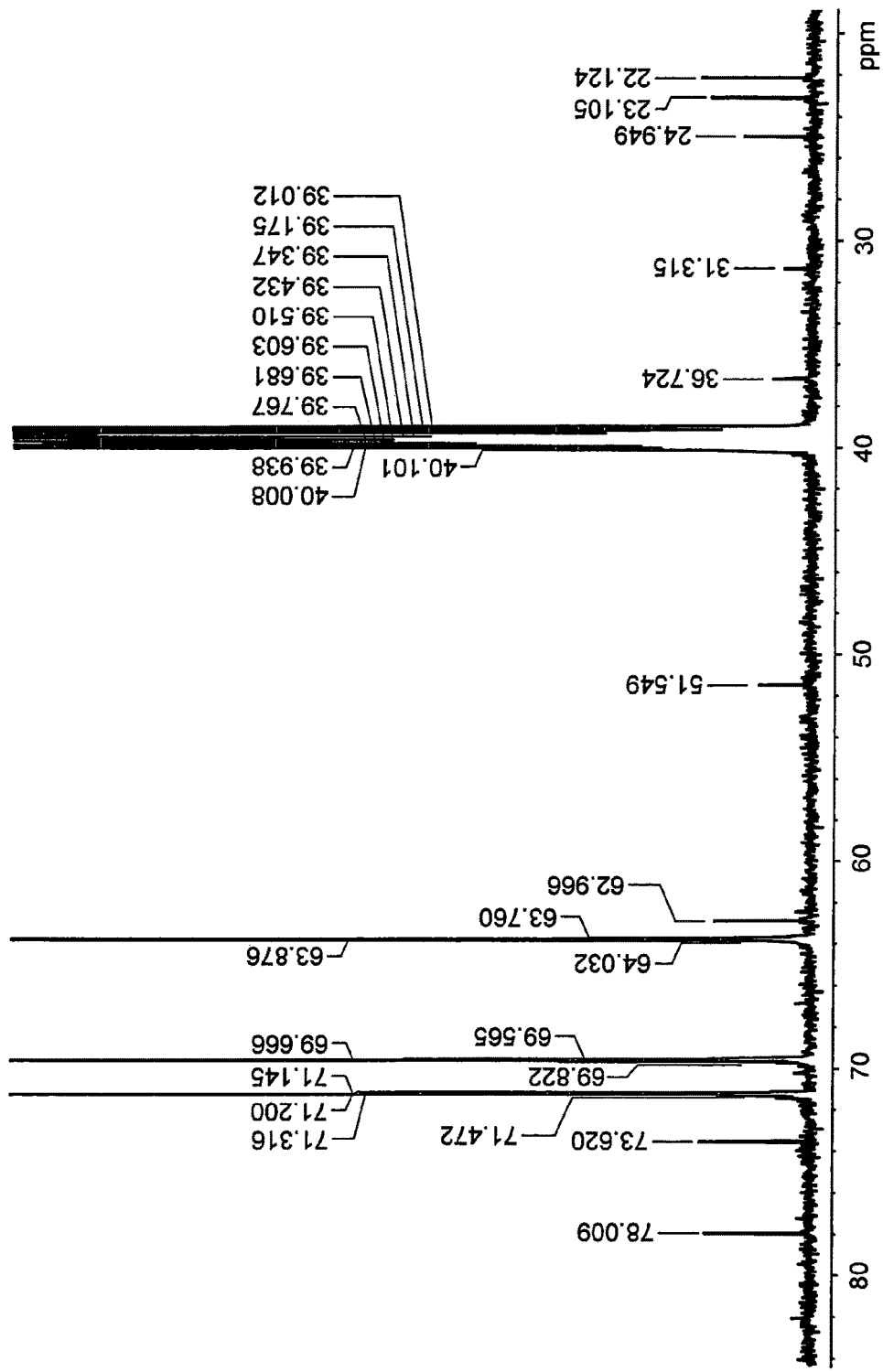
FIG. 4 shows the $^{13}$C NMR spectrum of a sample of bortezomib-mannitol ester commercially available as Bortenat, between 0 to 110 ppm.

Further, comparison of the $^{13}$C NMR spectra of the bortezomib-mannitol ester formed in accordance with the invention and generic Bortenat sample (in particular, comparison with FIGS. 3 and 4), shows that the $^{13}$C NMR spectrum of compound B matches with $^{13}$C NMR spectrum of lyophilized material of Bortenat sample. In particular, the $^{13}$C NMR Spectrum recorded in DMSO-d6 solvent shows that the characteristic peaks for bortezomib-mannitol ester, which include 63.1 ppm, 73.7 ppm and 78.1 ppm, are observed in both the bortezomib mannitol ester samples of compound B and the generic Bortenat sample. Tabulated below are the comparison results of bortezomib mannitol ester samples of compound B and generic Bortenat sample for ester confirmation.

| Source | | Compound B | Bortenat Injection sample |
|---|---|---|---|
| $^{13}$C Chemical shift (ppm) of three Extra peaks due to ester formation (—$CH_2$, —CH, —CH respectively). | —$CH_2$ | 63.09 | 62.96 |
| | —CH | 73.71 | 73.62 |
| | —CH | 78.10 | 78.00 |

The $^{13}$C NMR spectrum of compound B therefore matches with $^{13}$C NMR spectrum of lyophilized material of Bortenat Injection sample.

The NMR data shows that that boronic acid: boronic ester ratio of compound B (bortezomib-mannitol ester) is on lower side (0.07:1) as compared to the values of both commercially available VELCADE and Bortenat samples, thus confirming that the processes of the present invention provide bortezomib-mannitol ester which is superior over the prior art.

Example 8: Preparation of Bortezomib Mannitol Ester for Injection (3.5 mg Bortezomib/3.5 ml Vial)

Formula A
Compound B in 1:6 Ratio

| Ingredients | mg/ml | mg/vial |
|---|---|---|
| Mixture of bortezomib mannitol ester and mannitol, with 1:6 weight ratio of bortezomib to mannitol | 7.0 | 24.5 |
| Mannitol | 4.0 | 14.0 |
| Water for injection | q.s. to 1.0 ml | q.s. to 3.5 ml |

Formula B
Compound B in 1:5 Ratio

| Ingredients | mg/ml | mg/vial |
|---|---|---|
| Mixture of bortezomib mannitol ester and mannitol, with 1:5 weight ratio of bortezomib to mannitol | 6.0 | 21.0 |
| Mannitol | 5.0 | 17.5 |
| Water for injection | q.s. to 1.0 ml | q.s. to 3.5 ml |

Manufacturing Process
1. In a stainless compounding vessel, compound B was added to water and stirred at room temperature to dissolve.
2. To this clear filtrate was added mannitol under stirring and stirred.
3. Made up the volume with water for injection.
4. Filtered through 0.22 μm sterilizing grade filter.
5. Vials filled and partially stoppered. Placed filled vials in lyophiliser for lyophilisation.
6. After completion of lyophilisation, vials stoppered completely and sealed.

While the present invention has been described in terms of its specific embodiments and examples, they are not to be construed as limiting. It will be appreciated that the invention may be modified within the scope of the appended claims.

The invention claimed is:

1. A process for the preparation of bortezomib-mannitol ester (compound B),

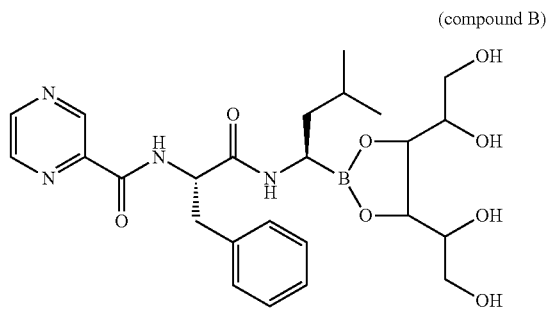 [SMILES: CC(C)C[C@H](NC(=O)[C@H](Cc1ccccc1)NC(=O)c1cnccn1)B1OC(C(O)CO)C(C(O)CO)O1]
(compound B)

comprising:
(a) dissolving bortezomib (compound A)

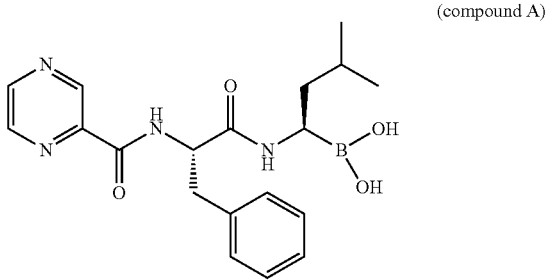 [SMILES: CC(C)C[C@H](NC(=O)[C@H](Cc1ccccc1)NC(=O)c1cnccn1)B(O)O]
(compound A)

in a first solvent to form a first solution wherein the first solvent comprises methylene dichloride, ethyl acetate or any combination thereof and wherein the first solution contains less than 1% water;
(b) adding mannitol to the first solution;
(c) removing the first solvent from the first solution to form a residue comprising bortezomib-mannitol ester;
(d) adding a second solvent to the residue to form a suspension of bortezomib-mannitol ester in the second solvent wherein the second solvent comprises n-heptane, hexane, toluene, cyclohexane, diisopropyl ether, diethyl ether, or any combination thereof; and
(e) isolating the bortezomib-mannitol ester from the second solvent.

2. The process according to claim 1 wherein the step (b) is carried out at a temperature of less than 35° C.

3. The process according to claim 1 wherein, after the mannitol is added to the first solution, the first solution is mixed for less than 30 minutes.

4. The process according to claim 1 wherein the mannitol is D-mannitol, and wherein the bortezomib-mannitol ester is bortezomib D-mannitol ester having the following structure

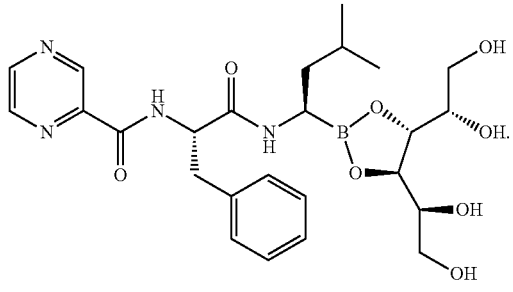 [SMILES: CC(C)C[C@H](NC(=O)[C@H](Cc1ccccc1)NC(=O)c1cnccn1)B1O[C@H]([C@@H](O)CO)[C@@H]([C@@H](O)CO)O1]

5. The process according to claim 1 wherein the first solution is free of water.

6. The process according to claim 1 wherein the removing of the first solvent in step (c) comprises evaporating the first solvent from the first solution.

7. The process according to claim 6 wherein the step of evaporating comprises subjecting the first solution to a temperature less than 30° C.

8. The process according to claim 6 wherein the step of evaporating comprises subjecting the first solution to a pressure less than 1 atmosphere.

9. The process according to claim 1 wherein the first solvent is not frozen prior to the step of removing the first solvent from the first solution.

10. The process according to claim 1 wherein the step of isolating comprises filtering the bortezomib-mannitol ester from the second solvent.

11. The process according to claim 1, further comprising sterilizing the first solution by filtration.

12. The process according to claim 11 wherein the first solution is filtered after step (a) and before step (b), and wherein said mannitol is sterile.

13. The process according to claim 11 wherein the filtration is carried out by passing the first solution through a sub-micron filter.

14. The process according to claim 11 wherein the filtration is carried out by passing the first solution through a first filter having a pore size less than 0.50 microns.

15. The process according to claim 11 wherein the filtration is carried out by passing the first solution through a second filter having a pore size less than 0.25 microns.

16. The process according to claim 1 wherein the step (b) is carried out at a temperature of less than 30° C.

17. The process according to claim 1 wherein, after the mannitol is added to the first solution, the first solution is mixed for less than 20 minutes.

18. The process according to claim 6 wherein the step of evaporating comprises subjecting the first solution to a temperature less than 25° C.

* * * * *